United States Patent [19]
König et al.

[11] Patent Number: 5,679,531
[45] Date of Patent: Oct. 21, 1997

[54] METHODS OF DETECTING βA4 PEPTIDE SPECIES ENDING AT CARBOXY-TERMINUS RESIDUE 42 USING MONOCLONAL ANTIBODY 369.2B

[75] Inventors: Gerhard König, Branford; Paul Graham, New Haven, both of Conn.

[73] Assignee: Bayer Corporation, West Haven, Conn.

[21] Appl. No.: 484,969

[22] Filed: Jun. 7, 1995

Related U.S. Application Data

[62] Division of Ser. No. 388,463, Feb. 14, 1995.

[51] Int. Cl.$^6$ .......................... G01N 33/53; C07K 16/18
[52] U.S. Cl. .................. 435/7.1; 435/7.92; 435/7.95; 435/40.5; 435/40.52; 530/387.9; 530/388.1
[58] Field of Search ................ 435/70.21, 240.27, 435/387.9, 7.1, 7.21, 7.9, 40.52, 40.5, 7.92, 7.95; 530/388.1, 358.2, 327; 436/548; 424/184.1, 185.1, 193.1, 194.1

[56] References Cited

FOREIGN PATENT DOCUMENTS

| | | |
|---|---|---|
| 0683234 | 11/1995 | European Pat. Off. . |
| WO A 91 16628 | 10/1991 | WIPO . |
| WO A 94 17197 | 8/1994 | WIPO . |

OTHER PUBLICATIONS

Motter et al., Ann. Neurol., 38:643–648, 1995.
Vigo-Pelfrey et al, Journal of Neurochemistry, 61:1965–1968, 1993.
Seubert et al, Nature 359:325–327, 24 Sep. 1992.
Joachim et al; Nature vol. 341 (6239): 226–230, 21 Sep. 1989.
Harlow et al "Antibodies:A Laboratory Manual", 1988 by Cold Spring Harbor Press Inc. pp. 626–631.
Iwatsubo et al, Neuron, 13: 45–53 Jul. 1994.
Glenner and Wong, "Alzheimer's disease: Initial report of the purification and characterization of a novel cerebrovascular amyloid protein" *Biochem. Biophys. Res. Comm.* 120: 885–890 (1984).
Master et al., "Amyloid plaque core protein in Alzheimer's disease and Down syndrome" *PNAS (USA)* 82: 4245–4249 (1985).
Miller et al., "Peptide compositions of the cerebrovascular and senile plaque core amyloid deposits of Alzheimer's disease" *Arch. Biochem. Biophys.* 301: 41–52 (1993).
Suzuki et al., "An increased percentage of long amyloid B protein secreted by familial amyloid B protein precursor ($BAPP_{717}$) mutants" *Science* 264: 1336–1340 (1994).
Yang et al., "Monoclonal antibody to the C–terminus of B–amyloid" *Neuro. Report* 5: 2117–2120 (1994).
Murphy et al., "Development of a monoclonal antibody specific for the COOH–terminal of B–amyloid 1–42 and its immunohistochemical reactivity in Alzheimer's disease and related disorders" *Am. J. Pathol.* 144: 1082–1088 (1994).

*Primary Examiner*—Marianne P. Allen
*Assistant Examiner*—Patricia A. Duffy
*Attorney, Agent, or Firm*—McDonnell Boehnen Hulbert & Berghoff

[57] ABSTRACT

The instant invention provides for monoclomal antibody 369.2B which is specific for the βA4 peptide, and in particular the free C-terminus of βA4 "1-42" but not "1-43", and stains diffuse and fibrillar amyloid, vascular amyloid, and neurofibrillary tangles. The instant invention further provides for antibody fragments and constructs thereof which have the same binding specificity. The instant invention also provides for methods of diagnosis, screening and therapeutics for treating unique forms of βA4 peptide, using the antibodies of the instant invention.

3 Claims, 10 Drawing Sheets

METHODS OF DETECTING βA4 PEPTIDE SPECIES ENDING AT CARBOXY-TERMINUS RESIDUE 42 USING MONOCLONAL ANTIBODY 369.2B This is a divisional of application Ser. No. 08/388,463 filed Feb. 14, 1995.

1. Field of the Invention

This application relates to Alzheimer's disease, particularly, to a monoclonal antibody specific for the βA4 peptide derived from Amyloid Precursor Protein, cells which produce such antibody, methods of generating such monoclonal antibodies, and to methods for using such antibodies in diagnostics and therapy.

2. Background

Alzheimer's Disease (AD) is an irreversible progressive neurodegenerative brain disorder. Over the course of several years the progression of AD leads to memory loss, dementia, and finally death. Currently, it is the fourth leading cause of death in the United States, accounting for approximately 100,000 deaths annually. Typically, AD affects primarily the elderly and is therefore, with the aging of modern society, expected to be an increasing health concern in the near future. Soon after the onset of the disease, patients require assistance around the clock. This represents a tremendous psychological as well as financial problem for our society. At present, no proven, means for diagnosis, prevention, treatment, or cure of AD exist.

Neuropathologically, AD is characterized by massive neuronal cell loss in certain brain areas, and by the deposition of proteinaceous material in the brains of AD patients. These deposits are the intracellular neurofibrillary tangles and the extracellular β-amyloid plaques. The major protein component of the β-amyloid plaque is the βA4 peptide. Sequence analysis of purified β-amyloid plaque material and mass spectrometry showed that the maximum length of the βA4 peptide is 43 amino acids. Typically, however, species of the peptide can also end either at position 40 or position 42 (Miller et al., 1993, *Arch. Biochem. Biophys.* 301:41–52). Similarly, at the N-terminus, a certain raggedness can be observed, leading to several different forms of the peptide, starting mainly at position 1, 4 or 11 (Miller et al., 1993).

Molecular cloning revealed that the βA4 peptide is derived from a much larger precursor protein termed the "Amyloid Precursor Protein" (APP) (Kang et al., 1987, *Nature* 325:733–736)(FIG. 1). FIG. 1 illustrates the Amyloid Precursor Protein (APP) which is a transmembrane (Tm= membrane region) protein where the N-terminus is located extracellular and the C-terminus is located intracellular (cytoplasmic). βA4 is partially embedded into the membrane. Several alternatively spliced isoforms have been described, which undergo extensive post-translational modifications (Selkoe, 1994, *Ann. Rev. Neurosci.* 17:489–517). The βA4 sequence itself is located partially on the extracellular side and extends partially into the transmembrane region (FIG. 2). FIG. 2 (SEQ ID NO:3) illustrates the βA4 sequence, shown (encircled area) extending with its C-terminal end into the transmembrane region (Tm, boxed area) and the N-terminal end located in the extracellular part. Asterisks indicate the location of familial mutations in the APP gene; they are either flanking the βA4 sequence, or are centered in the middle portion of the βA4 sequence. The three major cleavage sites (α, β and γ) in APP are indicated. Release of βA4 was therefore postulated to occur through the proteolytic action, of one or more proteases on the N-terminus (β-cut) and on the C-terminus (γ-cut) of the peptide (FIG. 2) (Selkoe, 1994). The main event during the secretion of APP is at the α-cut (position 16/17 of βA4 "1-42"). This secreted APP molecule (αAPPs) contains the first 16 amino acids of the βA4 sequence at its carboxyl end. The remaining cell-associated APP fragments (so called C-terminal fragments (CTF's)) contain the C-terminal portion of the βA4 sequence and extend to the cytoplasmic region of APP. Therefore, this proteolytic cut results in fragments which may not be processed in such a way that directly or indirectly leads to amyloidogenic fragments (non-amyloidogenic processing) (Selkoe, 1994).

Recently, it was demonstrated that cell lines which express large amounts of APP through a stably transfected APP cDNA construct produce high picomolar to low nanomolar amounts of βA4 and release it rapidly into the medium (Shoji et at., 1992, *Science* 258:126–129). It has also been found that virtually every primary cell culture and cell line releases βA4 constitutively (Busciglio et al., 1993, *PNAS USA* 90:2092–2096). Additionally, healthy controls as well as Alzheimer patients have been shown to have low nanomolar amounts of βA4 in sera and CSF (Seubert et al., 1992, *Nature* 359:325–327). The majority of the detected soluble βA4 species in these body fluids and conditioned media was βA4 "1-40", which is not truly reflective of the overall composition found in β-amyloid plaque depositions. The notion that the production and subsequent release of βA4 is sufficient and therefore responsible for the buildup of β-amyloid plaques in the brains of AD patients could therefore no longer be maintained; other factors must contribute to the deposition of β-amyloid plaques. One straightforward hypothesis is that acute or chronic overproduction of βA4 causes the increased amyloid load observed in AD The finding that specific point mutations in and around the βA4 region of the APP gene are linked with certain familial Alzheimer's disease (FAD) cases showed unequivocally that the APP gene is a "disease gene" (Goate et al., 1991, *Nature* 349:704–706; Murrell et al., 1991, *Science* 254:97–99; Levy et at., 1990, *Science* 248:1124–1126; Carter et al., 1992, *2Nature Genetics* 2:255–256). In families in which AD is inherited dominantly with a specific age of onset, the point mutations in the APP gene are necessary and sufficient to cause AD. A/though the vast majority of Alzheimer disease cases are sporadic and probably multifactorial, these familial APP mutations can teach us a great deal about amyloidogenesis, i.e., the generation of the small βA4 peptide from the larger precursor and its subsequent deposition in β-amyloid plaques.

The double mutation at APP codon 670/671 (the "Swedish variant", at the N-terminus of βA4 in APP) causes a 5 to 8 fold higher release of βA4 in cell cultures stably transfected with that mutated APP cDNA (FIG. 2) (Citron et al., 1992; Cai et al., 1993). It is conceivable that this double point mutation leads to an increased turnover of APP due to increased proteolysis at the β-cut, which in turn leads to a higher level of released βA4. Increased amounts of βA4 monomers, as demonstrated by transfection studies with the "Swedish mutation", can explain the faster kinetics of βA4 aggregation to β-amyloid plaques in these families.

Another FAD mutation lies C-terminal of βA4 at position 717 ("London variant") and does not affect the level of released βA4 in tissue culture (FIG. 2). It was recently demonstrated that this 717 mutation changes the "1-40/1-42" βA4 ratio (Suzuki et al., 1994, *Science* 264:1336–1340). Although it is not clear at the moment how the generation of the C-terminus of βA4 occurs, since this part is embedded in the transmembrane region, it is tempting to hypothesize that the "London mutation" affects the proteolytic breakdown of APP to βA4. Possibly, this point mutation interferes with the cleavage fidelity of the responsible protease at the γ-site. βA4 1-40 exhibits among other things a dramatic difference in its solubility in aqueous solutions when compared to βA4 1-42 (Burdick et al., 1992, *JBC* 267:546–554). The latter is virtually insoluble in water, whereas 1-40 is water soluble up to several mg/ml in vitro. Minor mounts of the longer 1-42 form can enhance precipitation of 1-40 in vitro dramatically. A slightly higher proportion of the longer 1-42 βA4 species would explain the early onset deposition of βA4 to β-amyloid plaques in patients with this "London mutation". The proportion of the 1-42 species to the shorter more soluble 1-40 species may also be one of the critical factors in the sporadic AD cases (i.e. cases where no genetic predisposition was identified). Monoclonal antibodies which specifically bind to the 1-42 species, are therefore useful to investigate the production and presence of βA4 species ending at amino acid position 42, and can be used as a diagnostic indicator of abnormal species present in AD.

Recent biochemical analyses with one antibody which recognizes βA4 ending at position 40, and one antibody recognizing βA4 species extending to position 42 or further, showed that the contribution of the longer βA4 species might be critical for the onset of the disease (Suzuki et al., 1994). However, the monoclonal antibody of Suzuki does not distinguish between βA4 1-42, 1-43, and longer βA4 species. This is also the case for another reported monoclonal antibody 2G9 (Yang et al., 1994, *Neuro Report* 5:2117–2120). Therefore, in order to avoid this crossreactivity, antibodies which are specific for βA4 species ending at position 42 m the exclusion of the other forms would be very useful in order to avoid crossreactivity with membrane associated C-terminal APP fragments, which are typical cellular products not necessarily associated with the β amyloid plaques.

One monoclonal antibody recognizing βA4 1-42 has been described (Murphy et al., 1994, *Am. J. Path.* 144:1082–1088). However, the βA4 1-43 peptide species was not used in these studies, thus it is not known what the exact specificity of this monoclonal antibody would be in response to the 1-43 peptide. Competition studies were only performed with βA4 peptides ending at position 40 ("1-40"), and position 44 (1-44) and beyond with this antibody. Importantly, the antibody was reported to stain diffuse amyloid, fibrillar amyloid, intraneuronal and extraneuronal neurofibrillary tangles, but not vascular amyloid.

An in vitro biochemical diagnostic test for Alzheimer's disease in its early stages as well as a means of screening for at-risk AD individuals is not available. The current diagnosis of AD requires a detailed clinical evaluation which cannot give clear answers until significant symptoms of dementia and memory loss are manifested. In view of the research referred to above, βA4 1-42 represents a preclinical marker for AD. Thus, identifying the level of or the buildup of βA4 1-42, or other residue 42 terminating species, and how this may progress during the course of the disease, and how it is distributed in the brain, will provide valuable insights into monitoring the course of, as well as for specific diagnosis and possible treatment of AD.

It would be useful for preparing diagnostic tests, therapeutics and for monitoring assays of AD, to have a monoclonal antibody which, in contrast to the specificity of presently available antibodies (crossreactive with 1-43; reported not stain vascular amyloid), does stain vascular amyloid and is specific for βA4 peptide ending at residue 42, and therefore extends the diagnostic capabilities of the art, i.e. one that recognizes the free C-terminus of βA4 1-42 and stains diffuse and fibrillar amyloid, neurofibrillary tangles, and vascular amyloid. Such an antibody is the subject of the present application.

SUMMARY OF THE INVENTION

The instant invention provides for monoclonal antibody which is specific for the βA4 peptide, and in particular, the C-terminus of βA4 "1-42" and stains diffuse and fibrillar amyloid, neurofibrillary tangles, and vascular amyloid. In particular, the instant invention provides for monoclonal antibody which is specific for all βA4 peptides in which the C-terminus is residue 42 of the βA4 amino acid sequence. The instant invention further encompasses antibody fragments and constructs thereof which have the same binding specificity. The instant invention encompasses in particular the monoclonal antibody known as "Mab 369.2B" and is produced by the cell line "369.2B" which has been deposited under the Budapest Treaty with the American Type Culture Collection (ATCC); Rockville, Md. on Jan. 26, 1995, and has been assigned the ascension number HB 11829. The instant invention encompasses the use of the monoclonal antibody of the instant invention in diagnostic, purification, and therapeutic uses.

Thus one embodiment of the instant invention encompasses a monoclonal antibody specific for βA4 peptide ending at position 42, wherein said antibody binds to diffuse amyloid, fibrillar amyloid, vascular amyloid, and neurofibrillary tangles. In one particular embodiment, the instant invention provides for a monoclonal antibody which is specific for the C-terminal amino acids of the βA4 1-42 peptide. In the most preferred embodiment the instant invention encompasses a monoclonal antibody that is identified as 369.2B, and is produced by the cell line deposited with the American Type Culture Collection (ATCC) as ascension number HB 11829. A preferred embodiment of the instant invention also encompasses a cell which is identified by the ATCC ascension number HB 11829. In a further embodiment of the instant invention, an immunologically reactive fragment of the monoclonal antibody of the instant invention which is capable of the same binding as the monoclonal antibody of the instant invention, is encompassed.

The instant invention also provides for methods of generating βA4 specific antibodies which recognize the free C-terminal residue 42. The instant invention also provides for methods for detecting the presence of βA4 peptides ending at position 42, in tissue comprising contacting a tissue sample with monoclonal antibody of the instant invention, by detecting the presence of monoclonal antibody in a selective fashion. The instant invention also provides for methods for selective purification of βA4 peptides ending at position 42, comprising contacting a sample to be purified with monoclonal antibody of the instant invention, separating the βA4 peptide from the sample to be purified, and isolating the βA4 peptide. In a further embodiment, the instant invention provides for methods for detection of βA4 peptide associated with Alzheimer's Disease, comprising contacting a sample to be tested with monoclonal antibody of the instant invention, and detecting the presence of βA4 peptides.

Thus the instant invention also provides for methods for the prevention of aggregation of βA4 peptide by administering monoclonal antibody of the instant invention. In a preferred embodiment the monoclonal antibody is identicle to 369.2B, or is an immunologically active fragment with equivalent binding specificity thereof. The instant invention thus provides a means for detecting the presence of βA4 peptide comprising an immunologically reactive fragment of the monoclonal antibody of the instant invention. As well as a means for preventing the aggregation of βA4 peptide comprising an immunologically reactive fragment of the monoclonal antibody of the instant invention. The instant invention provides a means for detecting and monitoring the level of βA4 peptide in tissue or fluid samples (e.g. blood, other body fluids, tissue sections, biopsy tissues etc.). In a preferred embodiment, the βA4 peptide being detected, monitored, inhibited or purified is a βA4 peptide with a free carboxy terminal amino acid residue being residue number 42 of the βA4 peptide amino acid sequence.

All references to publications and patent documents in the prior or subsequent sections are hereby incorporated by reference in the entirety. Specific preferred embodiments of the present invention will become more evident from the following more detailed description of certain preferred embodiments and the claims.

BRIEF DESCRIPTION OF THE DRAWINGS

The invention will be more completely understood from a consideration of the following detailed description, taken in conjunction with the drawings, in which.

DETAILED DESCRIPTION OF THE INVENTION

Figure 1:
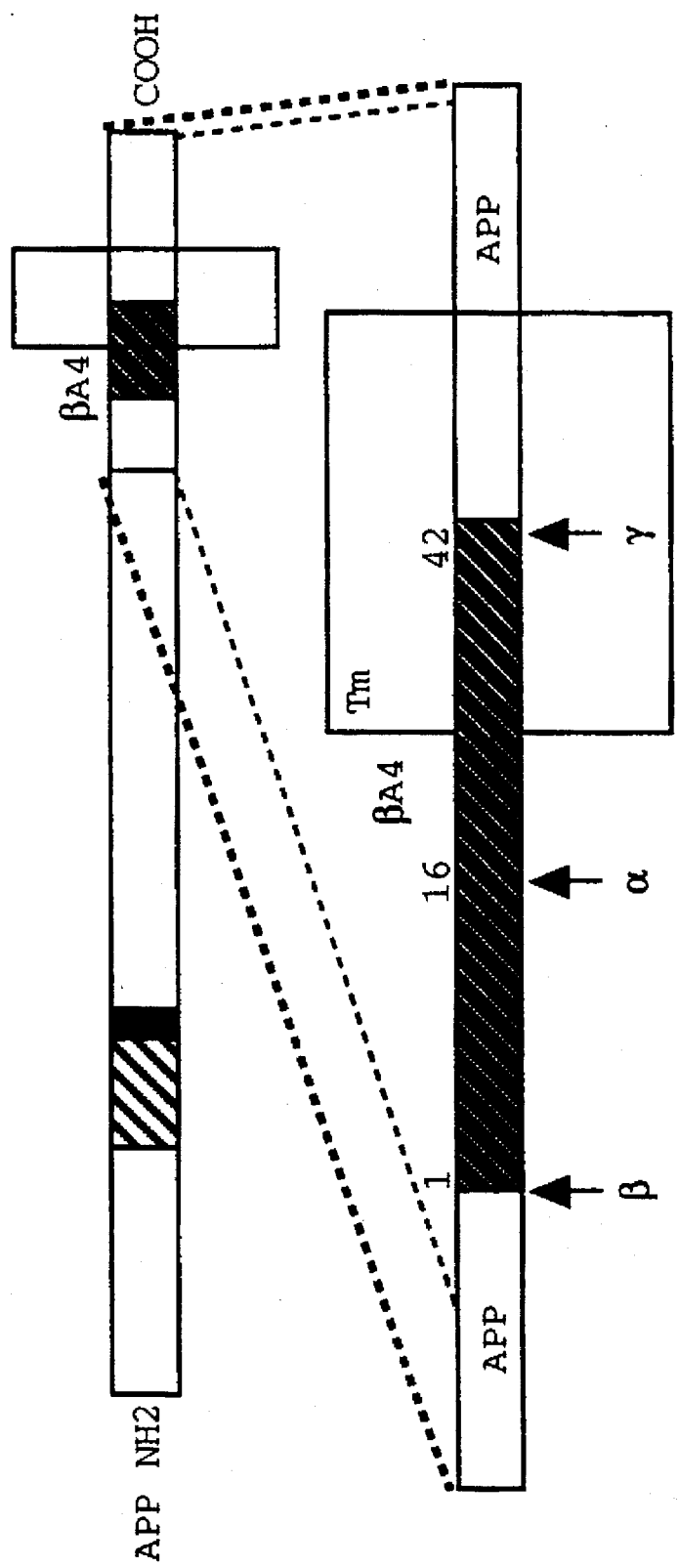
FIG. 1 is a schematic showing the βA4 portion of the Amyloid Precursor Protein (APP), its location relative to the cell membrane, and the α, β and γ cleavage sites.
Figure 2:
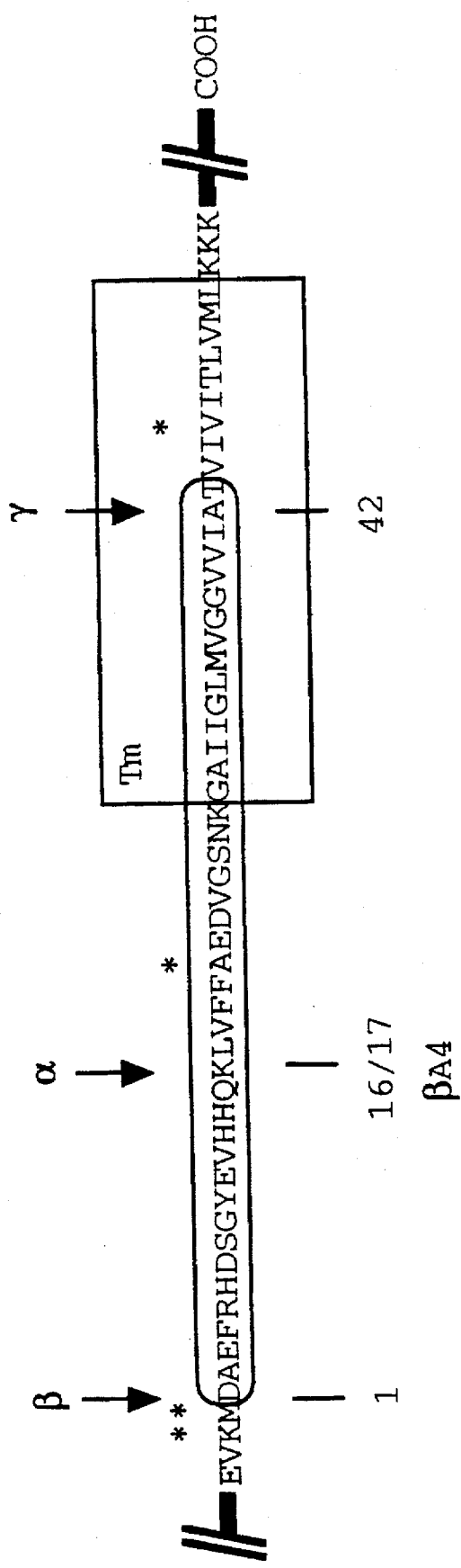
FIG. 2 shows the βA4 portion of APP, its position relative to the transmembrane region of a cell, and the three major cleavage sites (α, β and γ) in APP (SEQ ID NO:3)

The β-amyloid depositions in Alzheimer's disease brains are made up mainly of βA4 peptides which show both N- as well as C-terminal heterogeneity. The major C-terminal species, identified by peptide sequencing of β-amyloid purified from postmortem brain material, end either at position 40 or 42 of the βA4 peptide which is at most 43 residues long. In vitro experiments with synthetic βA4 peptides ending either at position 40 or 42 indicate profound physico-chemical differences. Previously, the distribution of these two βA4 species in postmortem tissue as well as their generation in vitro could not be addressed due to the lack of specific antibodies against the carboxy end capable of distinguishing between subspecies of βA4 peptide.

Recent evidence suggests that release of βA4 is a normal event in virtually every cell culture. Typically high picomolar to low nanomolar concentrations of βA4 can be measured in serum and cerebral spinal fluid (Seubert et al., 1993). This finding was surprising because it had been assumed that the production of βA4 is a pathological event since βA4 is massively deposited as β-amyloid plaques in the cortical and hippocampal brain regions of Alzheimer disease patients. Detailed sequence analysis of the released βA4 from cell culture revealed that the major species end at position 40 (Selkoe, 1994). Amyloid plaques purified from postmortem brain show a slightly different picture: amyloid deposits of the congophilic amyloid angiopathy (CAA) are βA4 aggregates surrounding blood vessels and are predominantly βA4 1-40, whereas in contrast amyloid plaques cores (APC) which are present in the brain parenchyma and are not associated with blood vessels exhibit an N-terminal raggedness (starting most commonly at residues 1, 4 and 11) and end mainly either at position 40 or 42 (Glenner and Wong, 1984, Biochem. Biophy. Res. Comm. 120:885–890; Masters et el., 1985, PNAS USA 82:4245–4249; Miller et al., 1993). Occasionally, longer species ending at 43 or extending even further have been described (Miller et el., 1993). Because the length of the-hydrophobic C-terminus is critical for the ability of the peptide to self-aggregate in vitro (Burdick et el., 1992; Jarrett et al., 1993, Biochem. 32:4693–4697), it is entirely possible that the two distinct pathological aggregates, APC and CAA and other vascular β-amyloid plaques, can be explained by the differing properties of the two species 1-40 and 1-42. This could also be the case for the so called "diffuse plaques" (Selkoe, 1994) which are seen frequently in brains of aged humans and are not associated with AD, however, have been proposed to be precursors of fibrillar β-amyloid deposits. A non-fibrillar aggregation of βA4 has been suggested for these structures. It is therefore of primary importance to determine the tissue specific production of these longer βA4 species (i.e., those ending at position 42) and their pathological appearance in brains of AD patients. Recently three reports have been published where antibodies have been described, which distinguish 1-42 and 1-40 species of βA4 (Suzuki et el., 1994; Murphy et al., 1994; Yang et el., 1994). Unlike the antibodies of the instant invention, the antibodies reported by Suzuki et el., and Yang et at., crossreact in a significant degree with both the 1-43 and 1-42 species of βA4 peptide. The antibody of Murphy etal., while not tested for binding with the 1-43 species of βA4 peptide, exhibits a different tissue binding pattern than the antibodies of the instant invention, and thus must recognize a different, or modified epitope from that recognized by the antibodies of the instant invention.

Positions 29 through 42 of the βA4 peptide lie entirely within the putative transmembrane region of the Amyloid Precursor Protein and are hydrophobic in nature (Miller et al., 1993). Synthetic peptides to the C-terminal sequences in this region must overcome the ability of the 34-42 sequence to form an unusually stable β-structure which is virtually insoluble in water and strong denaturants (Halverson et al., 1990, Biochem. 29:2639–2644) if they are to be used to elicit good immune responses against soluble βA4. We designed a hydrophilic spacer five residues long which would overcome those insolubility problems and also extend the presumed epitope away from the proximity of the carrier. To reduce the likelihood of cross-reactivity with the shorter but major βA4 species, 1-40, we chose a minimal peptidyl epitope of 8 residues corresponding to positions 35-42 of the βA4 sequence. The entire synthetic sequence designed in this way was coupled by a free sulfhydryl group on a N-terminal cysteine residue to KLH (keyhole limpet hemocyanin).

Successful use of spacers and hydrophilic residues in the production of antipeptide antibodies is well documented as is the use of hydrophilic structures to bring insoluble haptens into solution for conjugation (McMillan et al., 1983, *Cell* 35:859–863; Makela and Seppala, 1986, in *Handbook of Experimental Immunology, Volume 1: Immunochemistry*, Wier, D. M., editor. Blackwell Scientific Publications, Oxford. pp 3.1–3.13). The success of this method in producing specific antibodies may at least in part be attributed to the presence of a free charged carboxyl terminal, especially in context of a hydrophobic sequence, as terminal residues on peptide antigens give rise to significant proportions of antipeptide antibodies (Gras-Masse et a;., 1985, in *Synthetic Peptides in Biology and Medicine*, Alitalo, K. et al., editors, Elsevier, Amsterdam, p 105). This, along with the selective and novel use of a minimal βA4 sequence used as an immunogen maximized the probability of producing an antibody which could distinguish between βA4 species ending at positions 42 with those that do not. Although peptide competition studies did not fine map the antigenic determinant, βA4 sequences other than 1-42 were not effective in inhibiting binding. The fact that 1-42 did not totally compete with $^{35}$-methionine-labelled in vitro-translated βA4 may be due either to the particular properties of the molecule itself or to the fact that the 35-42 peptide immunogen was presented in the context of a specific spacer and/or carrier, or that a 200–1000 fold excess of unlabelled peptide is not enough to quench the signal. Non-specific effects of N-terminal residues on antigenic activity are also well documented (Benjamini et al., 1968, *Biochem.* 7:1261–1264).

The intriguing finding that 25-35 actually enhances the ability of 369.2B and other antibodies to bind to βA4 may be due to a peculiar interaction between the abstracted peptide and the full length βA4 sequence itself. Residues 26-33 are believed to exist as a random coil in aqueous solution (Halverson et al., 1990) and may be able to interact with soluble βA4 in such a way that makes the C- terminus more accessible to the binding sites on antibodies.

The highly specific antibody of the instant invention, of which 369.2B is a particular example was raised against a synthetic βA4 peptide having residues 35-42, and does not recognize the shorter βA4 species 1-40 in solution or on a solid phase. Furthermore, both 1-40 and 1-43 were unable to absorb out the antibody when used immunohistochemically. A secondary screening method with medium capacity through-put for the screening of hybridoma supernatants using radioactively labelled in vitro translated βA4 was applied so that antibodies culled from the primary screening could be further selected for their ability to immunoprecipitate soluble βA4. This method can be easily adapted to other proteins/antibodies of interest. The resulting MAb 369.2B represents a superior tool to investigate the role of βA4 peptides ending at position 42 in situ, postmortem tissue, transgenic animals, and the in vitro generation of βA4 peptides in established cellular βA4 production models, for diagnostic use, and for therapeutics.

The monoclonal antibody of the present invention represents an important tool needed to establish a diagnostic test kit. It permits one to measure/quantify the amount of the βA4 1-42 or derivatives thereof (e.g. 4-42 species, and other truncated forms with the "42" carboxy end) in human body fluids (CSF, serum, urine etc.) or tissues. It can also be used to study the distribution pattern of 1-42 or βA4 species ending in residue 42, in AD brains compared to healthy controls. Its exceptional high avidity makes it a superior and novel tool for such testing. The monoclonal antibody here disclosed can also be used in biological model systems such as transfected cell cultures or animal models (transgenic mice), designed to measure and/or influence the presence and/or production of βA4 species ending in amino acid 42. These model systems represent means to identify selective modulators of the production of βA4 ending in amino acid position 42 of the βA4 in biological systems. The antibodies of the instant invention provide for methods of preventing aggregation of βA4 peptide because the specificity of the antibody will allow for the specific interference with the free C-terminal residue, thereby interfering with and disrupting aggregation that may be pathogenic in AD.

Surprisingly, the antibody of the present invention differs from that of the prior art in that it stains diffuse and fibrillar amyloid, neurofibrillary tangles, and vascular amyloid while being specific for the βA4 peptide free C-terminal residue 42. This unique binding pattern shows that the antibody of the instant invention recognizes a different epitope from that of the prior art, and that the tissue distribution or accessibility of the βA4 peptide recognized by the antibody of the instant invention is also different. Further, the instant invention provides for monoclonal antibody which can precipitate the βA4 peptide out of solution, which was not demonstrated by the antibodies of the prior art. Thus the instant invention provides for unique monoclonal antibodies which recognize a unique subset of βA4 species which has a distinct tissue distribution that is most likely a better diagnostic indicator than what was previously available, and a unique target for therapeutic intervention.

Thus the instant invention provides for antibodies, antibody fragments and constructs thereof which are specific for the βA4 species of peptide where the C-terminal ends at residue 42. The instant invention also provides for the use of such antibodies, binding fragments and constructs thereof in diagnostic, analytic, therapeutic, and biochemical purification methods which employ the binding specificity of the instant monoclonal antibodies and their use within pharmaceutical formulations.

The following examples will further explain the instant invention and are shown by way of illustration, and not by way of limitation. The following examples illustrate certain aspects of the above-identified methods and compositions as well as advantageous results.

Example 1:βA4 Peptide Expression System
Preparation of plasmid pGK002

General cloning and molecular biology procedures are found for example in Sambrook, Fritsch, and Maniatis, 1989, *Molecular Cloning* 2nd edition, Cold Spring Harbor Lab Press. Plasmid pMTI-26, which is a Bluescript KS clone containing 2.415 kb (kilobase pairs) of the APP sequence with a TAG stop codon followed by a BamHI site placed in frame by site-directed mutagenesis after the 42nd amino acid codon of the βA4 region, was modified by excising a 1.8 kb Xba I/Bgi II fragment and religating the plasmid after filling in the ends. The resulting construct, designated pGK002, places the consensus coming initiation codon of the βA4 sequence immediately downstream of the Bluescript T7 promotor.

Preparation of plasmid pGK003

Figure 3:
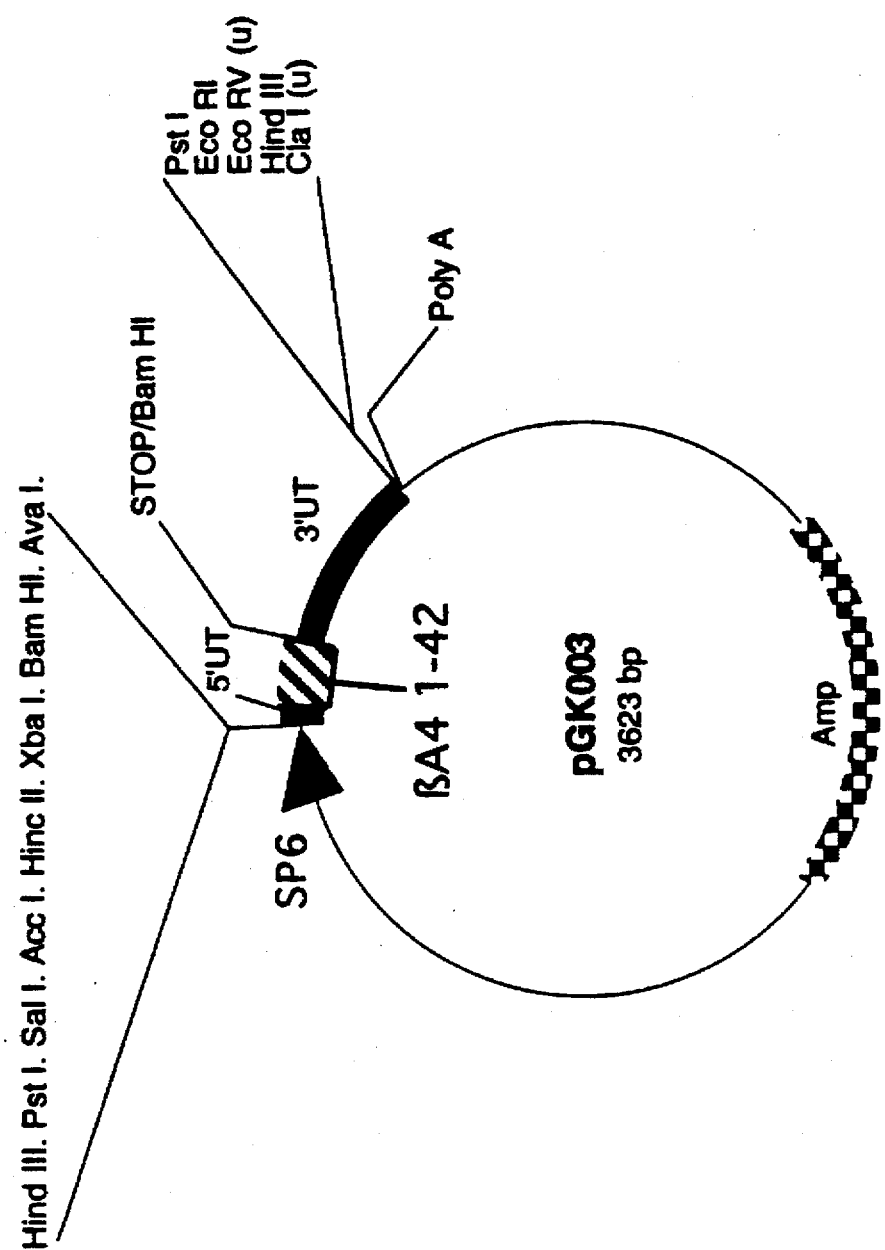
FIG. 3 is a diagram of the clone pGK003 which was used to generate the βA4 1-42 peptide.

Plasmid pGK003 (FIG. 3), used in all of the wheat germ in vitro translations of βA4 to be described below, was made by subcloning a 590 bp (base pair) NotI/Xho I fragment from pGK002 containing the entire human βA4 sequence with the mutagenized stop/Bam HI into a pSP64 polyA vector (Promega Corp.). In preparing this plasmid, pGK002 was digested with Not I and Xho I and the resulting 590 bp fragment was filled in with Klenow, isolated, and ligated with pSP64polyA linearized with Sma I. FIG. 3 is a diagram of Clone pGK003. The open reading frame of βA4 1-42 is expressed in vitro from the bacterial SP6 promoter. The 3'untranslated (3'-UT) region of APP is shown in black.

Example 2: In Vitro Transcription and Translation of pGK003

Plasmid pGK003 was linearized with EcoRV and complete digestion was confirmed by agarose gel electrophoresis. The sample was extracted twice with phenol/chloroform, followed by two chloroform extractions and ethanol precipitation. The resulting pellet was washed once in 70% ethanol, partially dried under vacuum, and resuspended in TE at a concentration of 1 μg/gl.

In vitro transcripts using linearized templates at 30 μg/ml were prepared in 80 mM HEPES-KOH (pH 7.5) buffer containing 16 mM $MgCl_2$, 2 mM spermidine, 40 mM DTT, 3 mM ATP/CTP/GTP/UTP, 800 units/ml RNAsin Ribonuclease Inhibitor (Promega Corp.), 5 units/mi Yeast Inorganic pyrophosphatase (Sigma Corp.), and 1800 units/ml SP6 RNA polymerase (Promega Corp.). The reaction mixture was kept at 37° C. for 4 hrs. The resultant transcript was verified by electrophoresis through a 1.2% agarose/TBE/EtBr gel with denatured samples (65° C.×10 min).

Transcripts were translated using Wheat germ extract (Sigma Corp.). Briefly, transcripts were heated (65° C.×10 min), mixed with the wheat germ extract containing KAc, RNAsin, and a methionine-minus amino acid mixture, and translated at 25° C. for 1 hr in the presence of $^{35}$-labelled methionine (Amersham). Translation of a 4 kD (kilo dalton) βA4 protein was verified by SDS-PAGE using 16% Tris/Tricine gel (Novex). Gels were fixed and proteins visualized fluorographically using a commercial system, "Amplify" (Amersham).

The incorporation of label into in vitro translated βA4, which contains one methionine residue per molecule, was determined by gel slicing. 2 mm slices were solubilized in 1 ml of 30% hydrogen peroxide, 0.75M $NH_4OH$ overnight at 37° C. Next a 10 ml volume of "Ready Value" scintillation cocktail (Beckman) was added and DPMs (Decay per minute) determined using a Beckman LS6000IC scintillation counter in the auto DPM mode. Typical reactions produce ~250 ng βA4/ml, or ~56 nM.

Figure 4A:
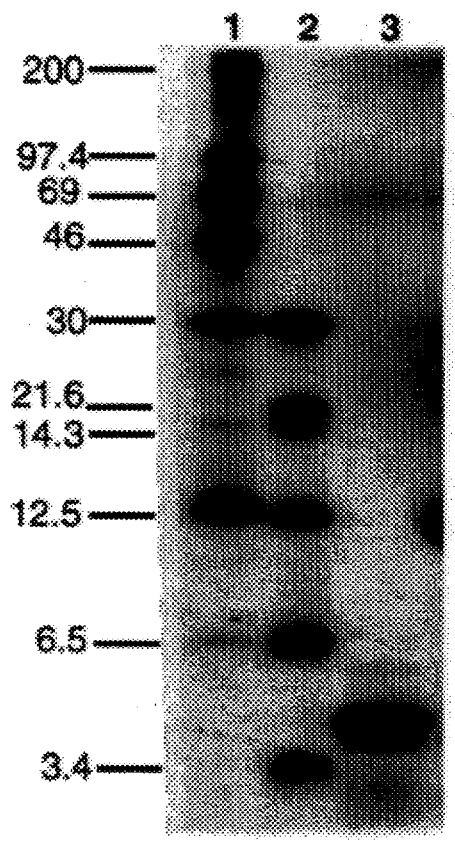
FIG. 4A shows SDS-PAGE on a 16% Tris/Tricine gel, of in vitro translated radioactively labelled βA4 in a wheat germ system.
Figure 4B:
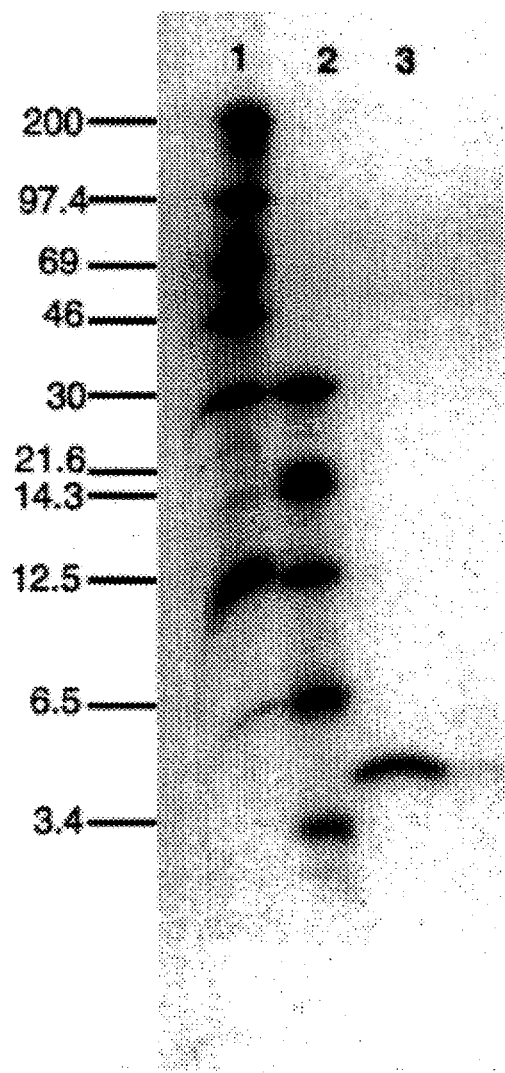
FIG. 4B shows SDS-PAGE on a 16% Tris/Tricine gel, of in vitro translated radioactively labelled βA4 from wheat germ system, immunoprecipitated with MAb 286.8A.

In vitro transcription followed by translation of the βA4 clone, pGK003, in a wheat germ system resulted in a single 4 kD protein product when visualized by fluorography on a 16% Tris-Tricine SDS polyacrylamide gel (FIG. 4A). FIG. 4A shows the results of SDS-PAGE on a 16 % Tris/Tricine gel. Lane 1: High MW markers. Lane 2: Low MW markers. Lane 3: In vitro translated βA4 in a wheat germ system. The identity of this 4 kD product was confirmed by immunoprecipitation with βA4 specific antibodies (FIG. 4B). FIG. 4B shows results of SDS-PAGE on a 16% Tris/Tricine gel. Lane 1: High MW markers. Lane 2: Low MW markers. Lane 3: In vitro translated βA4 from wheat germ system immunoprecipitated with MAb 286.8A. Transcription and translation of this as well as other βA4 clones in a combined reticulocyte lysate system (TnT) did not result in the same yield or purity of radioactively labelled βA4 (data not shown). This could be due to the short transcript or to the peculiar nature of the βA4 peptide itself.

Figure 5:
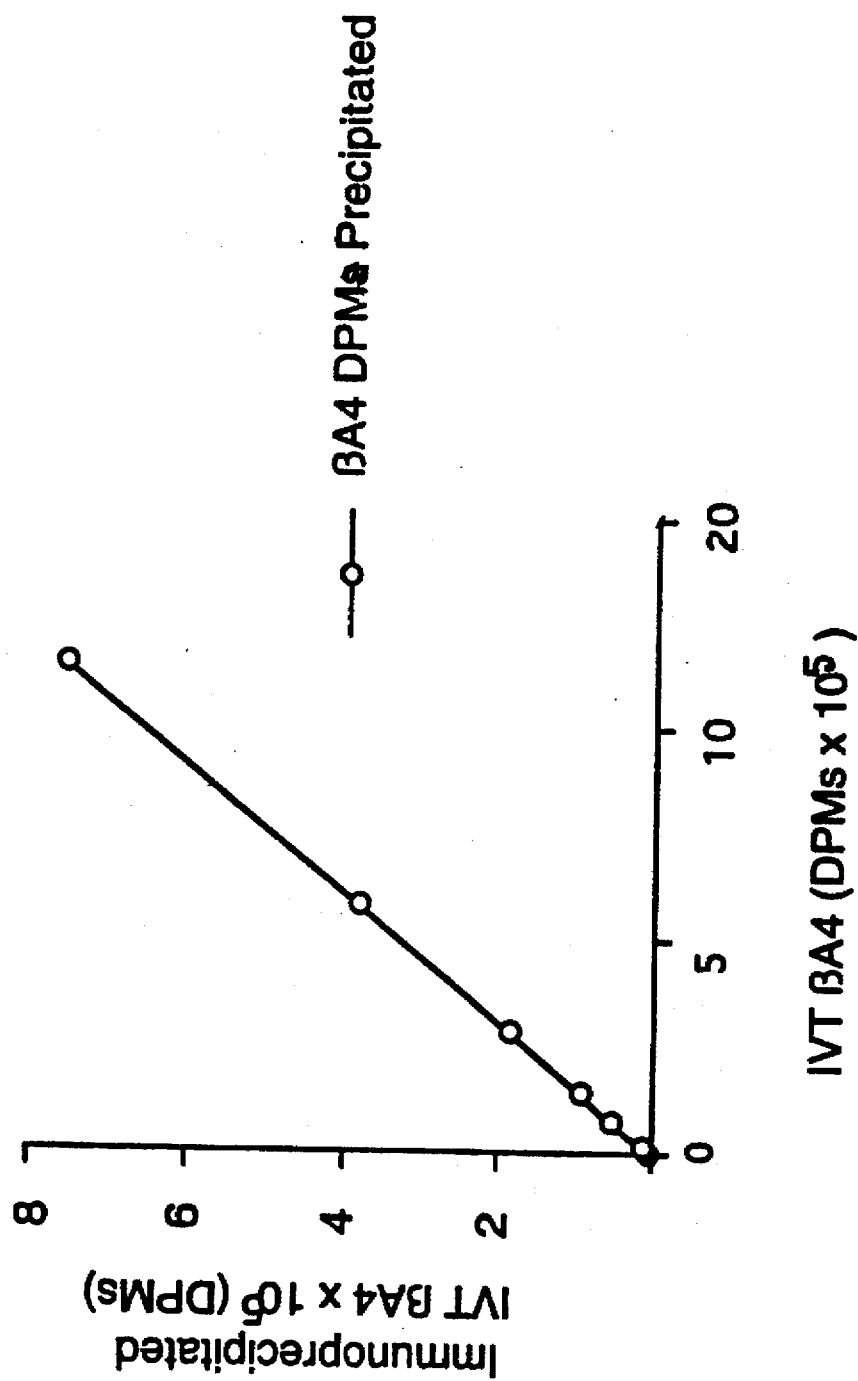
FIG. 5 is a graph showing immunoprecipitation of in vitro translated βA4 (IVT βA4) with 286.8A.

The monoclonal antibody 286.8A, which was raised against crude peptide 1-42 and maps to region 3-8 of βA4, was able to precipitate this protein in a concentration-dependent manner (FIG. 5). FIG. 5 graphs this immunoprecipitation of in vitro translated βA4 (IVT βA4). Increasing amounts of IVT βA4 were immunoprecipitated with a fixed amount of 286.8A (7.4 μg) in 100 gl in RIPA buffer.

Example 3: Immunogen and Screening Peptide Preparation

Peptides were prepared by standard Fmoc solid-phase procedures. (see for example Gras-Masse et al., 1985).

Peptide 959, a 14 residue synthetic peptide having an N-terminal cysteine attached to a hydrophilic DGDGD spacer and residues 35-42 of human βA4 (resulting complete sequence: CDGDGDMVGGVVIA (SEQ ID NO: 1)), was coupled to a maleimide-activated KLH (Keyhole Limpet Hemocyanin) carrier using the commercially available "Imject" Activated Immunogen conjugation kit (Pierce). Briefly, 2 mg of peptide were dissolved in 200 μl of conjugation buffer and allowed to react at room temperature for 2 hrs with 2 mg of reconstituted maleimide-activated KLH. The conjugate was purified by gel filtration and used as an immunogen for monoclonal antibody production using standard protocols as described in Example 4.

Peptide #958, a 14 residue synthetic peptide having an N-terminal cysteine attached to a GGGGG spacer and residues 35-42 of the human βA4, (resulting complete sequence: CGGGGGMVGGVVIA (SEQ ID NO: 2)), was coupled to ovalbumin by dissolving 2 mg of peptide in 200 μl 6M guanidine, 0.01M phosphate pH 7.0 and conjugated as above to 2 mg of a reconstituted maleimide activated ovalbumin. The purified conjugate was used in ELISA-screening of monoclonal fusion products. Antibodies screened in this way are specific for the "35-42" determinant rather than the spacer, cysteine bridge or carrier portions of the immunogen.

Figure 6A:
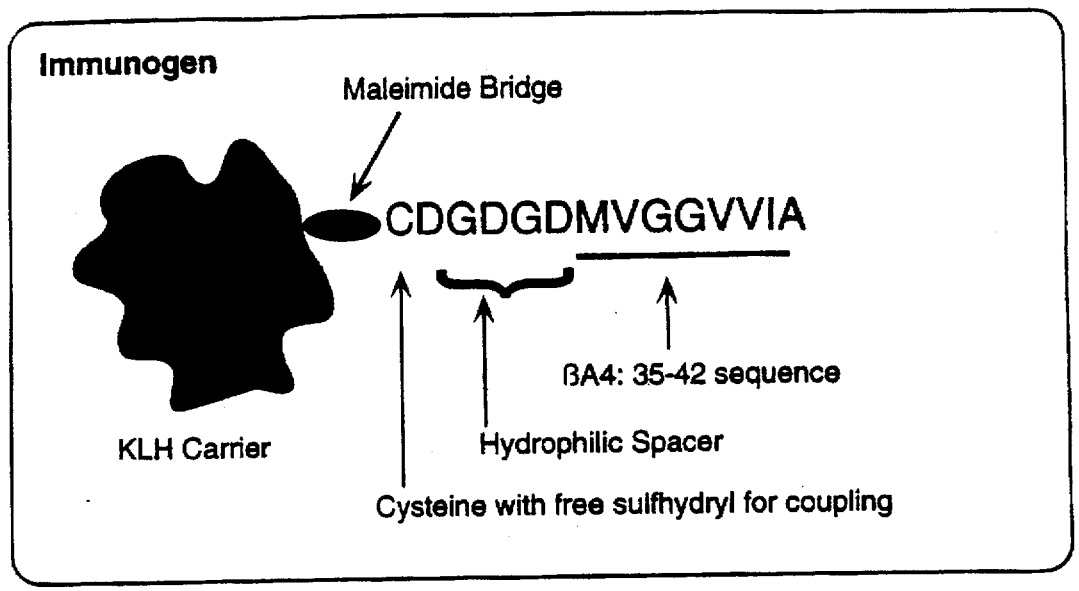
FIGS. 6A and 6B are diagrams of the peptides (SEQ ID NO:1 and SEQ ID NO:2) used to generate the immune response (immunogen) and to screen the sera of mice.
Figure 6B:
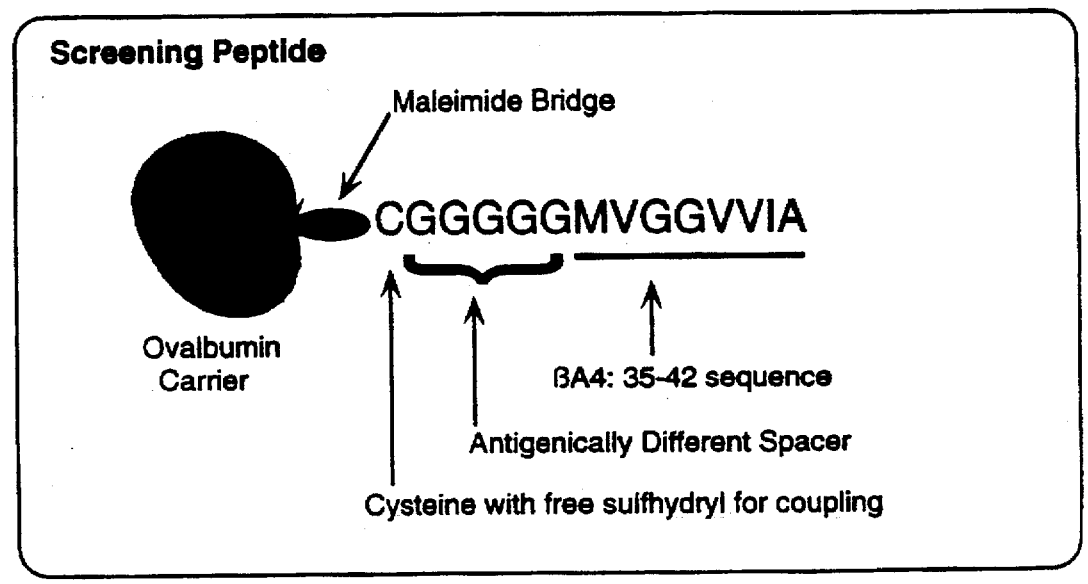

FIG. 6: Illustrates the peptide used to generate the immunresponse (the immunogen) and the peptide used to screen the sera of mice, as well as fusions, in the enzyme immunoassay plate (EIA) are shown. βA4 sequence 35-42 was synthesized together with a spacer and a C-terminal Cysteine, which was then used to couple it covalently via maleimide bridge to a large carrier molecule. Both, the spacer and the carrier molecule in immunogen and screening peptide are different in order to select for βA4 sequence specific antibodies.

ELISA (Enzyme Linked Immunosorbant Assay)

Biotinylation of MAb

The N-hydroxysuccinimide ester of biotin is used to biotinylate monoclonal antibody 286.8A. The integrity of the reagent is first verified by watching it's spontaneous hydrolysis in the absence of primary amines: an 0.2 mg/ml solution of NHS-LC-Biotin (Vector Labs, Burlingame, Calif.) in PBS is monitored at 260 nm over time. An OD260 of 1.0 after approximately 2 hrs (rising from and initial OD260~0.55) indicates the expected hydrolysis.

In the biotinylation reaction a 66:1 molar ratio of Biotin to monoclonal 286.8A at neutral pH has been found to give optimal results when the biotinylated 286.8A was tested in an Elisa format. NHS-LC-Biotin 0.6 mg in $H_2O$ at a concentration of 0.1 mg/ml is added (within 5 rain of dissolving) to 1 ml (2 mg) of 286.SA in PBS. Nucleophilic attack of the NHS ester is allowed to occur at 25 ° C. for 4 hrs after which 10 mg of glycine in 50 μl $H_2O$ is added to stop the reaction. The reaction is then placed over a 10 ml cross-linked dextran desalting column equilibrated to PBS and 0.5 ml aliquots are collected. The first peak representing the IgG peak is pooled and stored at 4° C. until used.

Elisa procedures

Corning 25801 96-well Elisa plates are coated overnight at 4° C. with 100 μl monoclonal 4G8 or other capture antibody at 5 μg/ml typically in $H_2O$ or buffer. The plate is then washed with PBS containing 1% Triton X-100 in a Dynatech Ultrawash plus. Wells are then blocked for 90 min with 300 μl PBS containing 1% Triton X-100 and 1% Elisa grade BSA (Blocking Buffer). After washing antigen or unknown diluted in blocking buffer is added to the wells in triplicates and incubated at room temperature for 2 hrs. The plate is washed 2 times and 400 ng biotinylated 286.8A or other detecting antibody is added. After 30 rain the plate is more extensively washed (2 times wash, 2 rain soak, 2 times wash) and 100 μl preformed Avidin-Biotin-Alkaline Phosphatase Complexes (Vector Labs) are added. The plate is washed (2 times wash, 2 rain soak, 2 times wash, 5 min soak, 4 washes) and MUP substrate added at 0.06 mg/ml 1×diethanolamine buffer. Plates are read in a Millipore Cytoflour after 15 min using a 360 nm excitation filter and a 460 nm emission filter.

Example 4: Generation of Monoclonal Antibodies

Balb/c mice were immunized with multiple I.P. inoculations of KLH conjagated peptide #959. Splenocytes from immunized animals were fused with the mouse myeloma AG8 using standard protocols (Wunderlich et al., 1992, J. Immunol. Methods 147:1–11). Supernatants from resultant hybridomas were screened for immunoreactivity to ovalbumin-coupled peptide #958 using standard Elisa protocols as described above. Hybridomas positive for the expression of immunoreactive MAbs were cloned at least twice by limiting dilution and MAb isotype analysis was performed. Purified MAb IgG was prepared from ascites fluid using protein-A affinity chromatography.

After fusion screening showed that immunization of mice with peptide #959 conjugated to KLH and screened in a solid-phase ELISA format with peptide #958 coupled to ovalbumin resulted in six positive parental signals (identified as 369.1 through 369.6). Both peptides have amino acids 35-42 of the βA4 region, different N-terminal spacers, and a cysteine for covalent coupling to carrier proteins (FIG. 6). The free C-terminus with the charged carboxy group and a limited length of only 8 amino acids favors the generation of antibodies which are specifically directed against longer forms of βA4 peptides; shorter βA4 peptides ending before amino acid 42 would thus not be recognized.

FIG. 6 diagrams the structure of the immunogen (carrier-peptide) and the screening peptide (carrier-screening peptide) used.

Two of the six parental signals were ultimately not clonable. Of the remaining four, two gave immunoprecipitation/scintillation signals only a few percent above normal non-immune controls; the other two (identified as 369.6 and 369.2) showed signals of 18% and 19% respectively. Production of monoclonal antibodies from ascites fluid and subsequent immunopurification of these clones was done. Table I compares the data obtained with the IPSA for hybridoma supernatants and purified antibodies.

TABLE I

| Cell Line | Isotype | IPSA (supernatant) | IPSA (purified) |
|---|---|---|---|
| 369.1 | IgG1/IgG2b | 3% | N.D. |
| 369.2 | IgG1 | 19% | 25% (with 5 μg) |
| 369.3 | IgG1 | 2% | N.D. |
| 369.6 | IgG2b | 18% | 7% (with 10 μg) |

Table 1. Comparison of antibody activities in hybridoma cell lines. IPSA data represents the percent of in vitro translated βA4 which could be immunoprecipitated by either hybridoma supernatants or purified antibody.

Example 5: Immunoprecipitation/Scintillation Assay for Hybridoma Screening

To develop and screen for monoclonal antibodies which recognize the βA4 peptide in solution rather than when attached to a solid phase, an assay was developed in which immunoprecipitation of an $^{35}$S-methionine-labelled in vitro-translated βA4 (IVT βA4) is measured. A standard amount of in vitro translated βA4 is allowed to form antibody/antigen complexes in a solution which can be optimized for ionic strength, pH, and detergent composition. After the immune complexes are precipitated with Protein G (Omnisorb cells) and washed extensively, bound radioactivity is counted in a liquid scintillation counter; background is subtracted and the efficiency of precipitation calculated. This Immunoprecipitation/Scintillation assay (IPSA) allows for both the rapid identification and characterization of antibodies, and has been used to test a variety of βA4 antibodies. The assay can be applied in general to monoclonal hybridoma supernatants as well as polyclonal sere to identify antibodies which can be used for immunoprecipitations. Typically 18 IPSAs can be performed in one day. This is therefore a fast and informative secondary hybridoma screening method.

Briefly, approximately 1.5×10$^5$ DPMs of $^{35}$-methionine-labeled in vitro-translated βA4 (IVT 1βA4) were added to 10 μl of a 10×immunoprecipitation buffer (150 nM NaCl, 10%NP-40, 5% deoxycholic acid; 1% SDS, 500mM Tris pH8). To this, 90 μl of monoclonal cell supernatant from the monoclonal fusion of interest (our designation #369) were added and allowed to react for 2 hrs at 4° C. Background was determined using 90 μl of supernatant of a non-reactive clone; the positive control was 90 μl of supernatant containing monoclonal antibody 286.8A which was made previously against a crude synthetic βA4(I-42) preparation. After 2 hrs, 40 μl of a 10% solution of Omnisorb cells (Calbiochem) equilibrated in 1× immunoprecipitation buffer (RIPA buffer; 150mM NaCl, 1%NP-40, 0.5% deoxycholic acid, 0.1% SDS, 50 mM Tris pHS) were added and allowed to react for an additional 2 hrs at 4° C. with rocking. The cells were pelleted by centrifugation for 5 rain at 4500 g and 4° C., and washed 3× with 800 μl cold 1×immunoprecipitation buffer. Pellets were quantitatively, transferred to scintillation vials and counted in a Beckman LS6000 scintillation counter in the Auto DPM mode. The percentage of βA4 immunoprecipitated was calculated.

Immunoprecipitation/Scintillation assays were performed with 1 μg of purified monoclonal antibody 369.2B in a total volume of 100 μl 1× immunoprecipitation buffer to which 5 μg of competing peptide were added. Incubations and precipitations were as described above.

Figure 7:
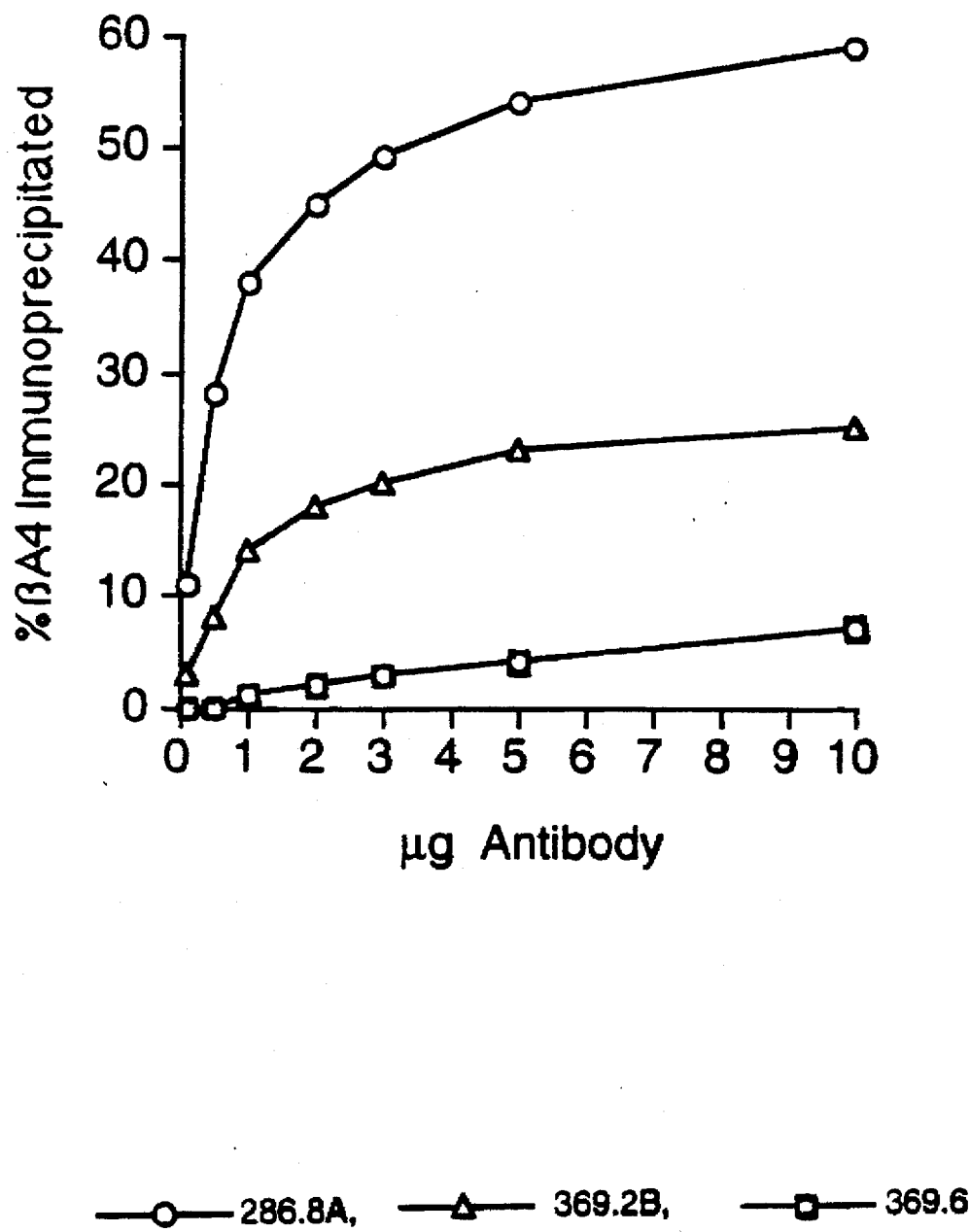
FIG. 7 is a graph showing immunoprecipitation of in vitro translated βA4 vs. antibody concentration; -○- 286.8A, -△- 369.2B, -□- 369.6.

FIG. 7 depicts the percentage of immunoprecipitated IVT βA4 as a function of antibody concentration for MAbs 369.2, 369.6 and MAb 286.8A. Under the conditions of this assay, 369.2 (and further subclone 369.2B) is approximately four times better than 369.6 in immunoprecipitating soluble IVT βA4, but precipitates a little less than half as much as 286.8. FIG. 7 shows the results of Immunoprecipitation of in vitro translated βA4 vs. antibody concentration (μg antibody/100 μl RIPA buffer) where;

Percent βA4 immunoprecipitated =

$$\frac{\text{(dpms with MAb)} - \text{(dpms with non or preimmune control)}}{\text{(total βA4 dpms/reaction)}}$$

Percents with a given MAb concentration varied only a few percentage points between and within experiments.

IPSA for Monoclonal Characterization

Approximately 1.5×10$^5$ DPMs of $^{35}$-methionine-labeled in vitro-translated βA4 were added to various amounts of purified monoclonal antibody, either 369.2B, 369.6, or 286.8A, in a total volume of 100 μl 1× immunoprecipitation buffer, and allowed to react as described above. Immune complexes were precipitated with Omnisorb, washed, and counted as described above.

Example 6: Characterization of MAb 369.2B

To further characterize the best cell line, 369.2B, a competition immunoprecipitation/Scintillation assay (Competition IPSA) was performed. In this variation 369.2B was added to an approximate 200 fold molar excess of unlabelled competitor peptide at the same time as labelled in vitro translated βA4 1-42. As expected, peptides to the human βA4 region, 1-40, 1-11, 1-28, 12-28, as well as the reverse peptide 40-1 did not compete with the $^{35}$-methionine-labeled in vitro-translated βA4 for immunoprecipitation, whereas the complete 1-42 peptide did (FIG. 8).

Figure 9:
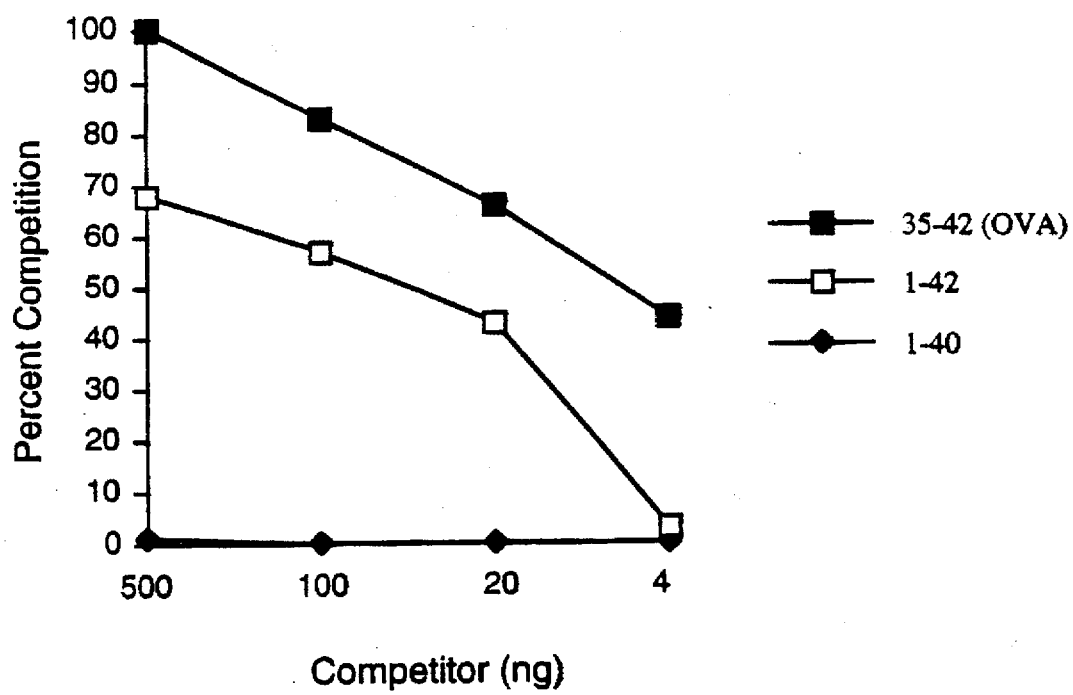
FIG. 9 is a graph showing epitope mapping of MAb 369.2 by competitive assay, with -■- being 35-42(OVA) (Ovalbumin coupled 35-42 βA4 peptide), -□- being 1-42 βA4 peptide, and -◆- being 1-40 βA4 peptide.

These results were corroborated in a solid-phase ELISA format: the absorbed ovalbumin-coupled screening peptide which contains the βA4 region 35-42, as well as the 1-42 peptide, compete whereas 1-40 did not (FIG. 9). The decreased competitiveness of the 1-42 peptide compared to the ovalbumin coupled 35-42 may be due to conformational and/or solubility factors involving the antigenic determinant, or perhaps more simply to the particular stoichiometry of the conjugation (ovalbumin, a carrier with molecular weight of 45 kD compared to 4 kD for the 1-42 peptide, and having somewhere between 5-15 conjugatable maleimide groups per mole of carrier).

Figure 8:
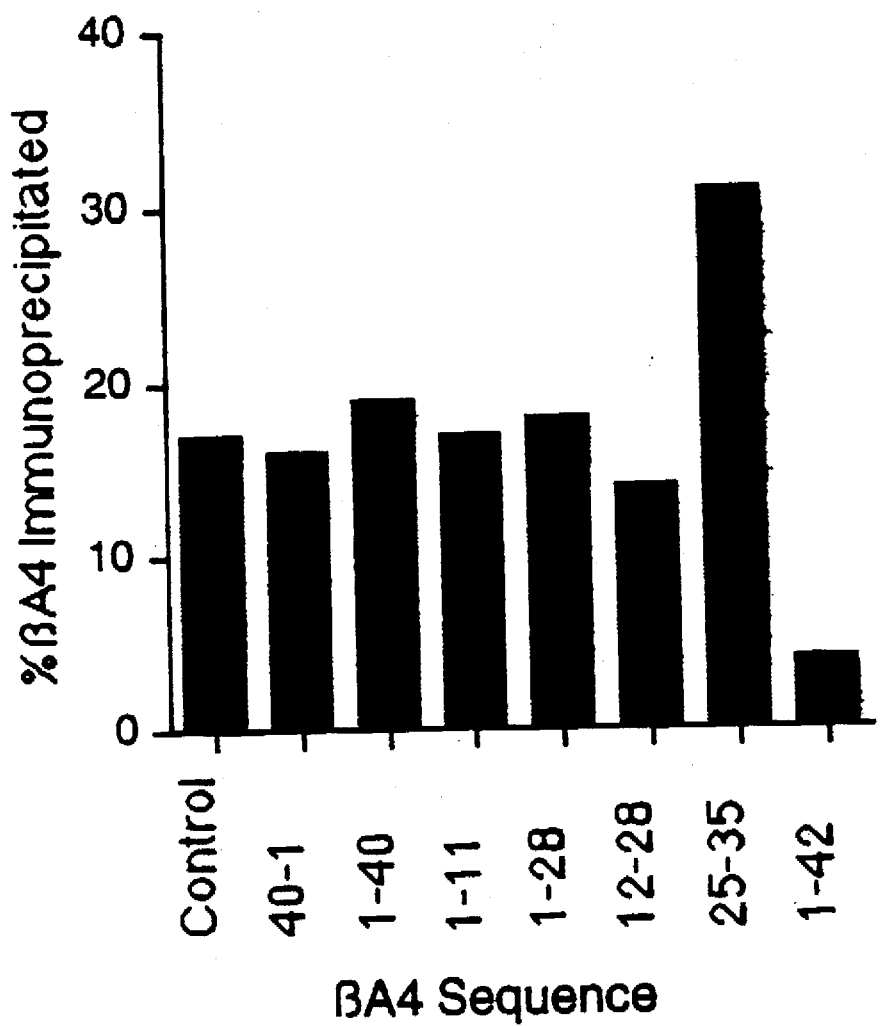
FIG. 8 is a graph showing the % of various βA4 sequences immunoprecipitated by MAb 369.2.

FIG. 8 shows Immunoprecipitation Peptide competition/Scintillation Assay for epitope determination of MAb 369.2. Peptide competitor (5 μg) was mixed with in vitro translated βA4 (~1.5×10$^5$ DPMs or ~200 pg) theft immunoprecipitated with 2 μg 369.2, where;

Percent βA4 immunoprecipitated =

$$\frac{(dpms\ with\ MAb) - (dpms\ with\ non\ or\ preimmune\ control)}{(total\ \beta A4\ dpms/reaction)}$$

Percents with a given MAb concentration varied typically only a few percentage points between and within experiments.

FIG. 9 shows epitope mapping of MAb 369.2 by competitive assay. C369.2 (50 ng IgG/100 μl) was preincubated with or without synthetic competitor peptides (22° C., 1 hr), then subjected to Elisa against plate-bound Ovalbumin-coupled 35-42 (200 ng/well). Percent competition was calculated relative to MAb binding in the absence of competitor, i.e. where;

$$\%\ competitor = \frac{(signal\ w/o\ competitor) - [(signal\ w\ competitor) - (background)]}{(signal\ w/o\ competitor)}$$

The solid square is 35-42(OVA) peptide conjugate; the open square is 1-42 peptide; and the solid diamond is 1-40 peptide.

From this data we conclude that monoclonal 369.2B is specific for the C-terminal end of the full length (1-42) βA4 peptide. Although the exact antigenic determinant has not been fine mapped, it clearly involves residues beyond position 40 and, singe the antibody was made to a short synthetic peptide the determinant is unlikely to involve other residues of βA4 which may be conformationally juxtaposed. Specifically, 369.2B is a very important tool in recognizing βA4 species ending at position 42.

One additional and interesting observation from the peptide competition assay is the enhanced immunoprecipitability of in vitro-translated βA4 by the decapeptide 25-35. This phenomena has also been seen in assays using one other monoclonal antibody (i.e., 286.8A) as well as one rabbit polyclonal antisera (data not shown). We also know from other experiments using varying amounts of detergent, specifically SDS, in IPSA assays with MAb 286.8A, that more βA4 can be immunoprecipitated with increasing amounts of detergent (data not shown). SDS, interestingly, has been shown to be ineffective in solubilizing βA4 aggregates, at least as shown by SDS-PAGE (Burdick et al., 1992). However it is not immediately clear why SDS should enhance the immunoprecipitability of βA4.

Example 7: Immunohistochemical Studies

We have undertaken immunohistochemistry studies with 369.2B. The staining pattern of 369.2B (1/10,000 dilution of a 22 mg/ml ascities purified antibody solution) when compared to the monoclonal antibody 286.8A which we have shown recognizes epitope 3-8 of βA4 and is human specific (data not shown) showed interesting differences. Results obtained from immunohistochemistry demonstrated that 369.2B is an excellent antibody (at $^{1}/_{10,000}$ dilution) to specifically label amyloid plaques cores, diffuse as well as fibrillar amyloid deposits and vascular amyloid deposits (FIG. 10).

Figure 10:
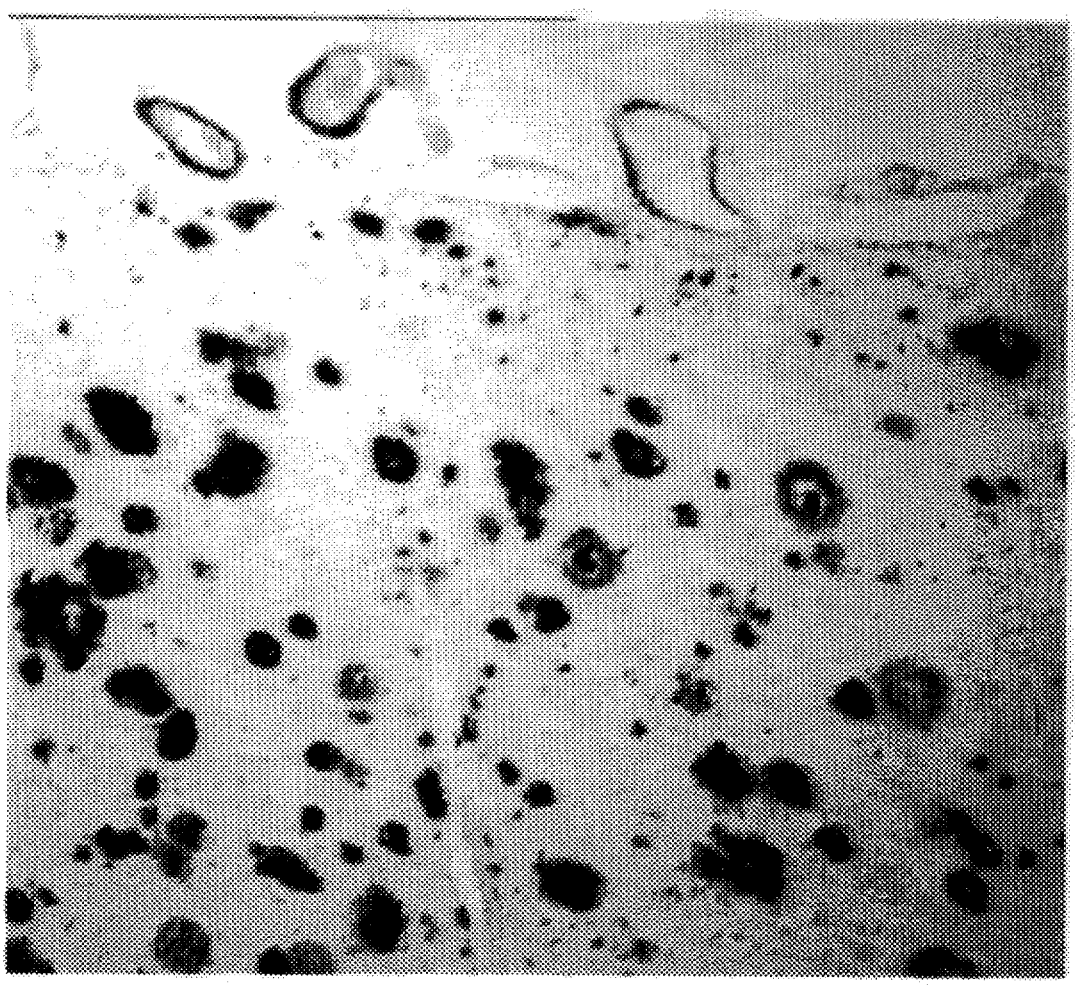
FIG. 10 is a photograph showing the binding of MAb 369.2B to vascular amyloid and other plaques with various morphologies.

FIG. 10 is a photomicrograph showing β-amyloid plaques, blood vessels, and perivascular deposits of βA4 in a paraffin embedded 10 μm thick section from the brain of a 76 year old female patient with Alzheimer's disease. Tissue sections were pretreated with 88% formic acid (30 rain), then labeled using an avidin-biotin-peroxidase kit (Vector Laboratories, Burlington, Calif.) with nickel-diaminobenzidine as the chromagen. Monoclonal antibody 369.2B labels plaques with a variety of morpologies, including cored, perivascular, and diffuse; (non-amyloidotic) plaques. It also labels a subset of amyloidotic blood vessels.

Further studies also showed that βA4 1-43 peptide was not able to compete for staining (more than a 1000 fold excess peptide), whereas βA4 1-42 completely abolished the signal (Table 2). Again as expected, 1-40 or 40-1 did not compete for staining. From these studies we can already conclude that this antibody is an excellent tool for immunohistochemistry. As suggested by in vitro studies which show physico-chemical differences between 1-40 and 1-42, it is possible that these two βA4 species show distinct patterns in Alzheimer brains. With-the monoclonal antibody of the instant invention, we are now able to begin addressing this question. Thus the monoclonal antibody and methods of the instant invention are useful for diagnostic and therapeutic uses in all immunological and related methodologies which can be applied to the detection, monitoring, extraction, inhibition and modification of unique BA,4 species, in the diagnosis and treatment of AD.

TABLE 2

| | Monoclonal Antibody used for Staining | |
|---|---|---|
| Competing peptide | N-terminal Mab 286.8A | C-terminal Mab 369.2B |
| None/buffer | +++ | +++ |
| None/DMSO | +++ | +++ |
| Human "40-1" | +++ | +++ |
| Human "1-16" | – | +++ |
| Mouse "1-16" | +++ | +++ |
| Human "1-40" | – | +++ |
| Human "1-42" | – | – |
| Human "1-43" | – | +++ |
| Human "35-42" with spacer | +++ | – |

Table 2. Results from competition binding experiments and inhibition of staining, a +++ indicates strong staining, – indicates no detectable staining.

It should be understood that the foregoing disclosure emphasizes certain specific embodiments of the invention and that all modifications or alternatives equivalent thereto are within the spirit and scope of the invention as set forth in the appended claims.

We claim:

1. A method of specifically detecting the presence of βA4 peptide species ending at carboxy-terminus residue 42 (alanine) in tissue, comprising contacting a tissue sample with monoclonal antibody 369.2B or binding fragment thereof to specifically bind said peptide, and detecting the presence of specifically bound monoclonal antibody 369.2B or binding fragment thereof, wherein the monoclonal antibody is produced by ATCC hybridoma 11829.

2. A method of specifically detecting in a sample the presence of βA4 peptide species ending at carboxy-terminus residue 42 (alanine) in diffuse amyloid, fibrillar amyloid, neurofibrillary tangles, and vascular amyloid deposits, comprising contacting a sample to be tested with monoclonal antibody 369.2B or binding fragment thereof to specifically bind said peptide, and detecting the presence of specifically bound monoclonal antibody 369.2B or binding fragment thereof, wherein the monoclonal antibody is produced by ATCC hybridoma 11829.

3. A means for selectively detecting the presence of βA4 peptide species ending at carboxy-terminus residue 42 (alanine) comprising an active βA4 peptide-binding fragment of monoclonal antibody 369.2B, wherein the monoclonal antibody is produced by ATCC hybridoma 11829.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Cys  Asp  Gly  Asp  Gly  Asp  Met  Val  Gly  Gly  Val  Val  Ile  Ala
1                  5                        10
```

( 2 ) INFORMATION FOR SEQ ID NO:2:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Cys  Gly  Gly  Gly  Gly  Gly  Met  Val  Gly  Gly  Val  Val  Ile  Ala
1                  5                        10
```

( 2 ) INFORMATION FOR SEQ ID NO:3:

( i ) SEQUENCE CHARACTERISTICS:
        ( A ) LENGTH: 59 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Cleavage-site
        ( B ) LOCATION: 4..5
        ( D ) OTHER INFORMATION: /label=Beta
            / note="Beta cleavage site in APP"

( i x ) FEATURE:
        ( A ) NAME/KEY: Cleavage-site
        ( B ) LOCATION: 20..21
        ( D ) OTHER INFORMATION: /label=Alpha
            / note="Alpha cleavage site in APP, residues 16/17 of BA4."

( i x ) FEATURE:
        ( A ) NAME/KEY: Cleavage-site
        ( B ) LOCATION: 46..47
        ( D ) OTHER INFORMATION: /label=Gamma
            / note="Gamma cleavage site in APP"

( i x ) FEATURE:
        ( A ) NAME/KEY: Peptide
        ( B ) LOCATION: 5..47
        ( D ) OTHER INFORMATION: /label=BA4
            / note="BA4 peptide"

( i x ) FEATURE:
    ( A ) NAME/KEY: Region
    ( B ) LOCATION: 33..56
    ( D ) OTHER INFORMATION: /label=Tm
        / note="Transmembrane region of APP"

( i x ) FEATURE:
    ( A ) NAME/KEY: Region
    ( B ) LOCATION: 1..32
    ( D ) OTHER INFORMATION: /label=Ex
        / note="N-terminal extracellular part of APP"

( x i ) SEQUENCE DESCRIPTION: SEQ ID NO:3:

```
Glu Val Lys Met Asp Ala Glu Phe Arg His Asp Ser Gly Tyr Glu Val
 1               5                  10                      15

His His Gln Lys Leu Val Phe Phe Ala Glu Asp Val Gly Ser Asn Lys
            20                  25                  30

Gly Ala Ile Ile Gly Leu Met Val Gly Gly Val Val Ile Ala Thr Val
        35              40                      45

Ile Val Ile Thr Leu Val Met Leu Lys Lys Lys
    50              55
```